(12) United States Patent
Ouchi

(10) Patent No.: US 9,063,055 B2
(45) Date of Patent: Jun. 23, 2015

(54) X-RAY IMAGING APPARATUS

(75) Inventor: Chidane Ouchi, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 269 days.

(21) Appl. No.: 13/610,365

(22) Filed: Sep. 11, 2012

(65) Prior Publication Data
US 2013/0070895 A1  Mar. 21, 2013

(30) Foreign Application Priority Data

Sep. 15, 2011 (JP) ................. 2011-201819

(51) Int. Cl.
| G01N 23/04 | (2006.01) |
| A61B 6/00 | (2006.01) |

(52) U.S. Cl.
CPC .......... *G01N 23/04* (2013.01); *G01N 2223/313* (2013.01); *G01N 2223/3301* (2013.01); *A61B 6/484* (2013.01)

(58) Field of Classification Search
CPC ...................................... A61B 6/484
USPC .......... 378/62, 70, 82–85, 91, 98; 359/10, 11, 359/204.5, 211.6, 279, 337.21, 563, 566; 356/334, 902, 903
See application file for complete search history.

(56) References Cited

U.S. PATENT DOCUMENTS 7,486,770 B2 * 2/2009 Baumann et al. ............... 378/62

FOREIGN PATENT DOCUMENTS

| JP | 2007203066 A | 8/2007 | |
| WO | WO-2010/146498 | * 12/2010 | ............... G02B 5/18 |

* cited by examiner

*Primary Examiner* — Robert Kim
*Assistant Examiner* — Eliza Osenbaugh-Stewar
(74) *Attorney, Agent, or Firm* — Canon USA Inc. IP Division

(57) ABSTRACT

An X-ray imaging apparatus for imaging a subject includes a diffraction grating configured to form an interference pattern by diffracting X-ray radiation from an X-ray source, a shielding grating configured to shield part of the interference pattern, a detector configured to detect the X-ray radiation passing through the shielding grating, and a moving unit configured to change an angle between each of the diffraction grating, the shielding grating and the detector and an optical axis, wherein the detector is configured to detect the X-ray according to a change in the angle between each of the diffraction grating, the shielding grating and the detector and the optical axis.

15 Claims, 18 Drawing Sheets

X-RAY IMAGING APPARATUS

BACKGROUND OF THE INVENTION

1. Field of the Invention

The present invention relates to an X-ray imaging apparatus for obtaining an X-ray phase image of a subject, and a wavefront measurement device for measuring a transmission wavefront of X-ray radiation transmitted through the subject using the X-ray imaging apparatus.

2. Description of the Related Art

Phase contrast imaging based on a phase difference of X-ray radiation caused by irradiating a subject with X-rays has been performed since 1990s. Japanese Patent Application Laid-Open No. 2007-203066 corresponding to U.S. Pat. No. 7,486,770 discusses an X-ray phase contrast method (hereinafter referred to as "X-ray Talbot interferometry") using the so-called Talbot interference. The X-ray Talbot interferometry includes an X-ray radiation source for generating X-ray radiation, a diffraction grating for diffracting the X-ray and forming an interference pattern (hereinafter referred to as a self-image) from a Talbot effect, and an X-ray detector for acquiring an X-ray intensity distribution. When a subject is arranged between the X-ray source and the diffraction grating or between the diffraction grating and the detector, the self-image is modulated by the subject. When the self-image modulated by the subject is detected by the detector, information of the subject can be obtained.

Further, generally, since the self-image has a very small period, it may be difficult to directly detect the self-image. An arrangement of a shielding grating in a position in which the self-image is formed has been discussed. The shielding grating shields a part of the X-ray forming self-image to form a moire. When the moire is detected by a detector, information of the subject can be obtained. A phase grating for modulating a phase may be generally used as the diffraction grating. In the phase grating, phase reference portions and phase shift portions are periodically arranged. The phase shift portion has such a thickness that the phase of the X-ray is shifted by a desired amount when the X-ray is incident on the phase shift portion.

Meanwhile, in the shielding grating, transmission portions that transmit an X-ray and shielding portions that shield the X-ray are periodically arranged. The shielding portion has a sufficient thickness to shield an incident X-ray.

Thus, in the diffraction grating and the shielding grating, the phase shift portions or the shielding portions each having the thickness necessary for their functions are arranged at a fine pitch. Accordingly, the phase shift portion and the shielding portion have a large aspect ratio (i.e., height/width, where the width is the length of the phase shift portion or the shielding portion in the array direction, and the height is the length of the phase shift portion or the shielding portion in the thickness direction of the grids.) Further, in order to increase an imaging range, it is necessary to use a large diffraction grating and a large shielding grating. In the diffraction grating or shielding grating, the X-ray is obliquely incident on the phase shift portion or shielding portion which creates a larger aspect ratio in an area away from the optical axis. Accordingly, the intended functions of the diffraction grating or shielding grating may not be performed and contrast of the formed self-image or moire may be increasingly degraded according to a size of the diffraction grating or shielding grating and the aspect ratio of the phase shift portion or the shielding portion. As a result, measurement accuracy of X-ray phase contrast is degraded as the area is away from the optical axis.

Japanese Patent Application Laid-Open No. 2007-203066 corresponding to U.S. Pat. No. 7,486,770 discusses a method for coping with it, in which a phase shift portion of a diffraction grating and a shielding portion of a shielding grating is processed to be directed to an X-ray source to be in parallel to an incident X-ray, instead of being orthogonal to a grating surface. In the diffraction grating and the shielding grating discussed in Japanese Patent Application Laid-Open No. 2007-203066 corresponding to U.S. Pat. No. 7,486,770, since the phase shift portion and the shielding portion need be directed to a specific direction that depends on a position within a grating surface, fabrication is not easy.

SUMMARY OF THE INVENTION

The present invention is directed to an X-ray imaging apparatus capable of improving contrast of a moire in an area away from an optical axis over an X-ray imaging apparatus of related art even when a diffraction grating and a shielding grating in which phase shift portions and shielding portions are orthogonal to grating surfaces are used.

The diffraction grating and the shielding grating in which the phase shift portions and the shielding portions are orthogonal to the grating surfaces are more easily fabricated as compared to the diffraction grating and the shielding grating discussed in Japanese Patent Application Laid-Open No. 2007-203066 corresponding to U.S. Pat. No. 7,486,770.

According to an aspect of the present invention, an X-ray imaging apparatus for imaging a subject includes a diffraction grating configured to form an interference pattern by diffracting X-ray radiation from an X-ray source, a shielding grating configured to shield a part of the interference pattern, a detector configured to detect the X-ray radiation passing through the shielding grating, and a moving unit configured to change an angle of each of the diffraction grating, the shielding grating and the detector with respect to an optical axis, wherein the detector is configured to detect the X-ray radiation passing through the shielding grating according to the change in the angle between the optical axis and at least one of the diffraction grating, the shielding grating and the detector.

Further features and advantageous aspects will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Figure 1:
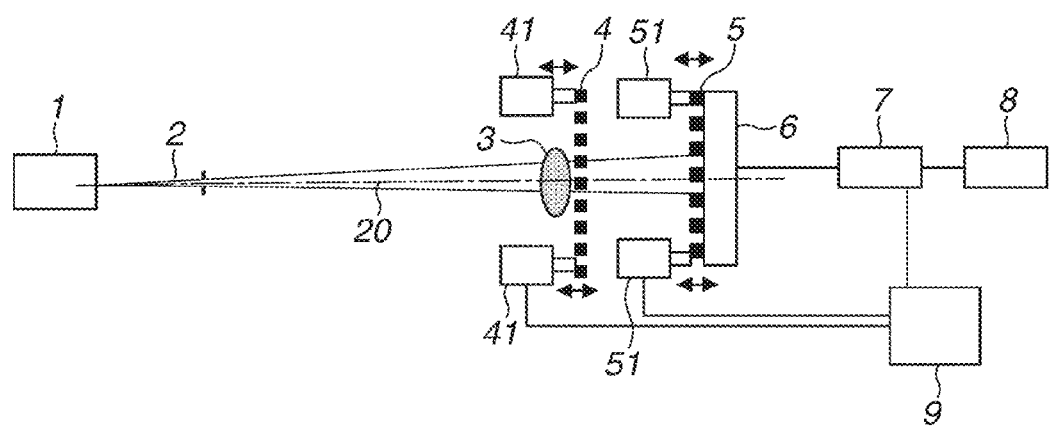
FIG. 1 is a diagram illustrating an X-ray imaging apparatus according to a first example of the present invention.

Various exemplary embodiments, features, and aspects of the invention will be described in detail below with reference to the drawings.

In each figure, the same reference numerals are assigned to the same members and a repeated description will be omitted. A first exemplary embodiment will be described. In order to achieve the above object, the first exemplary embodiment has the following characteristics. An X-ray imaging apparatus of the present exemplary embodiment includes an X-ray source, a diffraction grating for diffracting an X-ray from the X-ray source to form an interference pattern, a shielding grating for shielding a part of the interference pattern, and a detector for detecting the X-ray passing through the shielding grating. In addition, in the present exemplary embodiment, the shielding grating and the detector are fixed. Further, the X-ray imaging apparatus of the present exemplary embodiment includes an actuator connected to the diffraction grating and an actuator connected to the shielding grating as a moving unit for changing an angle between each of the diffraction grating, the shielding grating and the detector and an optical axis. The actuator connected to the diffraction grating changes the angle between the diffraction grating and the optical axis by moving the diffraction grating. Meanwhile, the actuator connected to the shielding grating changes an angle between each of the shielding grating and the detector and the optical axis by moving the shielding grating and the detector fixed to the shielding grating. In addition, in this description, the optical axis (an X-ray axis) refers to a center of a light beam (an X-ray beam). Further, the detection result of the detector is analyzed by a calculator to calculate information of a subject.

Hereinafter, each configuration will be described. The X-ray source of the present exemplary embodiment may be an X-ray source that outputs a continuous X-ray or may be an X-ray source that outputs a characteristic X-ray. Further, a ray source grating or a wavelength selection filter for dividing the X-ray into narrow beams may be arranged on a path of the X-ray output from the X-ray source. In this description, when the ray source grating or the wavelength selection filter is used, the ray source grating or the wavelength selection filter is regarded as a portion of the X-ray source. Since the X-ray output from the X-ray source need be diffracted by the diffraction grating to form an interference pattern, spatial coherence that can form an interference pattern is required. Further, the X-ray output from the X-ray source is a divergent X-ray. In addition, in this description, the X-ray refers to electromagnetic radiation having energy equal to or greater than 2 KeV (thousand electron volts) and equal to or smaller than 100 keV. When an X-ray beam output from the X-ray source is transmitted through a subject, the phase of the beam's wavefront is changed according to a refractive index and a shape of the subject. To that end, the subject may be arranged between the X-ray source and the diffraction grating or may be arranged between the diffraction grating and the shielding grating.

The diffraction grating of the present exemplary embodiment is a phase-type diffraction grating (hereinafter also referred to as a phase grating), and receives a divergent X-ray beam to form a self-image (an interference pattern) in which bright portions and dark portions are periodically arranged. The diffraction grating may be an amplitude-type diffraction grating, but the phase-type diffraction grating is advantageous since a loss of the X-ray amount is less. The phase grating of the present exemplary embodiment is a two-dimensional phase grating in which phase shift portions and phase reference portions are arranged in two directions orthogonal to each other, and which receives an irradiated X-ray to form a two-dimensional interference pattern. An X-ray transmitted through the phase shift portion has undergone a certain amount of phase shift, as compared to an X-ray transmitted through the phase reference portion. In general, a phase grating having a phase shift amount of $\pi$ radian or $\pi/2$ radian is often used, but a phase grating having a shift amount of other values may be used. A material of the phase grating is advantageously a material having a high X-ray transmittance, such as silicon.

Further, the phase grating is connected to an actuator and rotated about a point on the phase grating as a center by the actuator. Accordingly, an angle between the phase grating and the optical axis is changed. The shielding grating of the present exemplary embodiment is a two-dimensional shielding grating in which transmission portions that transmit an X-ray and shielding portions that shield (block partially or totally) the X-ray are two-dimensionally periodically arranged. That is, the shielding portion may not completely shield the X-ray. However, it is necessary to shield the X-ray to the extent that a moire is formed as an interference pattern is overlaid with a shielding grating. A period of the shielding grating may have the same or slightly different value as or from a period of the interference pattern formed on the shielding grating by the diffraction grating and can be determined according to a period of a moire desired to be formed. In addition, the moire in this description includes a moire having a period of an infinite length or a moire having a period close to the infinite length.

In general, since a period of the self-image formed by X-ray Talbot interferometry is finer than spatial resolution of a general X-ray detector, it is difficult to directly detect the self-image. A shielding grating having a slightly different period from the self-image is used or a shielding grating having the same period as the self-image is slightly rotated within a shielding grating surface to thereby generate a moire having a greater period than the self-image, which is acquired by a detector. Since the moire keeps a pattern change of the self-image by the subject, information about a change in the self-image by the subject can be obtained by analyzing the moire acquired by the detector, using mathematical methods in a calculator.

A distance $Z_1$ between the phase grating and the shielding grating satisfies the following equation (1) representing a Talbot condition so that a clear self-image is generated on the shielding grating.

$$\frac{1}{Z_0} + \frac{1}{Z_1} = \frac{1}{N}\frac{\lambda}{d^2} \qquad (1)$$

Where $Z_0$ is a distance between the X-ray source and the phase grating, $\lambda$ is a wavelength of the X-ray radiation, and d is a grating period of the phase grating. Among one-dimensional phase gratings in which phase reference portions and phase shift portions are one-dimensionally arranged, in the case of a phase grating whose phase shift amount is $\pi/2$ (hereinafter referred to as a $\pi/2$ phase grating), N is a real number represented by n−½. In the case of a phase grating whose phase shift amount is $\pi$ (hereinafter referred to as a $\pi$ phase grating), N is represented by real number of n/4-⅛. Where n is a natural number. In a phase grating in which phase reference portions and phase shift portions are arranged in a shape of checkerboard pattern, N is n/2-¼ in the $\pi/2$ phase grating and n/4-⅛ in the $\pi$ phase grating. In this case, the grating period d is twice the distance between a center of the phase reference portion and a center of the phase shift portion.

However, for example, when a distance between the phase grating and the detector increases or a detector having fine spatial resolution is used, the self-image can be directly detected by the detector. When the self-image is directly detected by the detector, the shielding grating is unnecessary, and the detector is arranged in a position satisfying the Talbot condition so that a clear self-image is generated on the detector. Accordingly, in Equation (1) described above, the distance between the phase grating and the detector may satisfy $Z_1$, and when the shielding grating is used, the detector may be arranged in a position in which the shielding grating is arranged. The shielding grating is also connected to the actuator similar to the phase grating, and the shielding grating is rotated about a point on the shielding grating as a center to thereby change an angle between the shielding grating and an optical axis.

The detector has an imaging element (e.g., a charge coupled device (CCD) sensor) capable of detecting an intensity distribution of a moire by the X-ray. Further, the detector of the present exemplary embodiment is fixed to the shielding grating in a state in which the detector is kept in parallel to the shielding grating. The detector is rotated about a point on the detector as a center by the actuator connected to the shielding grating to change an angle between the detector and the optical axis. That is, the angle that the detector makes with respect to the optical axis can be changed with the actuator. Therefore, since the detector is fixed to the shielding grating and the detector is kept in parallel to the shielding grating, the detector performs detection of the X-ray according to a change in an angle between each of the diffraction grating, the shielding grating and the detector with respect to the optical axis.

The calculator calculates information about a change in the moire by the subject based on a moire detection result of the detector. As a result, for example, a phase image or a differential phase image of the subject can be obtained. Further, an image display unit may be connected to the calculator to display an image on the image display unit based on the calculation result.

An example of a mathematical method to calculate information about a change in the moire using a calculator will be now described. When an X-ray passes through the subject, a phase of the X-ray is changed according to a refractive index distribution of the subject. A spatial distribution of the phase change of the X-ray is a phase image of the subject. A traveling direction of the X-ray is proportional to spatial differentiation of the phase of the X-ray, and a positional change of the pattern of the self-image is proportional to a traveling direction change of the X-ray. Accordingly, if a Fourier transform method is used for the X-ray intensity distribution detected by the detector, spatial differentiation of the phase image of the subject (hereinafter referred to as a differential wavefront) can be obtained. Since details of the Fourier transform method are well known, for example, as discussed in Mitsuo Takeda et al., "Fourier-transform method of fringe-pattern analysis for computer-based topography and interferometry", J. Opt. Soc. Am., Vol. 72, No. 1 (1982), an overview will only be described herein. In a frequency spectrum obtained by subjecting the intensity distribution, which is a detection result of the detector, to two-dimensional Fourier transform, peaks corresponding to a frequency (hereinafter referred to as a carrier frequency) of a basic periodic component of the intensity distribution (hereinafter referred to as a carrier pattern) and a number of harmonic components of the basic periodic component are generated. The vicinity of the peak corresponding to the carrier frequency is cut out and moved to a center of a Fourier space. Further, it is subjected to inverse Fourier transform and a phase component is obtained from a result of the inverse Fourier transform to obtain a differential wavefront in one direction of a wavefront to be measured, i.e., a differential phase image of the subject. In order to restore the phase image of the subject, this differential phase image is integrated in a differential direction. However, usually, only with this, it is difficult to calculate a change in the wavefront in a direction orthogonal to the differential direction. This can be resolved by performing the same process on the other peak and obtaining a differential wavefront in two directions orthogonal to each other. In addition, the calculation method using a calculator is not limited to the method shown above and, for example, may be a method using window Fourier transform or a method using a phase shift method (a fringe scanning method).

Figure 2:
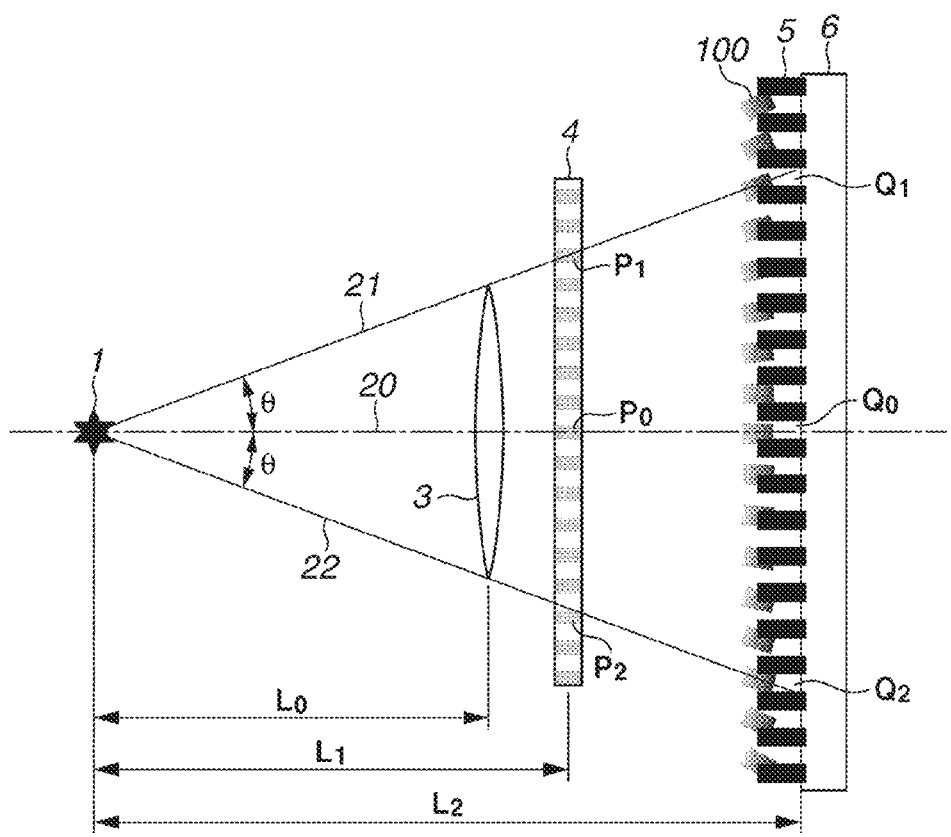
FIG. 2 is a diagram illustrating a principle of a first exemplary embodiment of the present invention.
Figure 3:
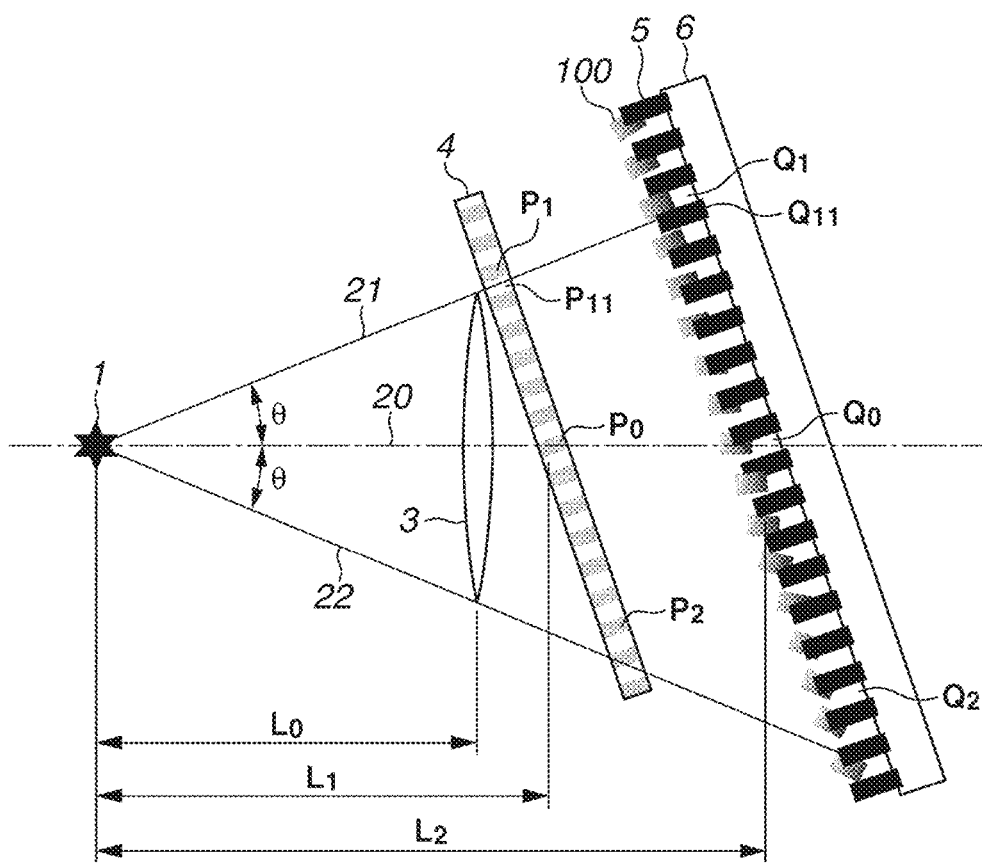
FIG. 3 is a diagram illustrating a principle of the first exemplary embodiment of the present invention.

Rotation of the phase grating, the shielding grating and the detector and a change in an angle between each of the diffraction grating, the shielding grating and the detector and the optical axis by an actuator connected to the phase grating and an actuator connected to the shielding grating, which are the moving units, will be described with reference to FIGS. 2 and 3. Further, in the present exemplary embodiment, the actuators connected to the phase grating and the shielding grating are used to move the phase grating, the shielding grating and the detector. However, since this is unnecessary to describe a principle, a description will be omitted. In FIGS. 2 and 3, the X-ray from the X-ray source 1 is transmitted through the subject 3, and the X-ray transmitted through the subject 3 is diffracted by the phase grating 4 to thereby form a self-image 100 on the shielding grating 5. A part of the self-image 100 formed on the shielding grating 5 is shielded by the shielding portion of shielding grating 5 to form a moire, which is detected by the detector 6. Further, the phase grating 4, the shielding grating 5, and the detector 6 are arranged so that a center of each X-ray irradiation area coincides with an intersection between the optical axis 20 and each of the center of the phase grating 4, the shielding grating 5 and the detector 6. Also, each of the phase grating 4, the shielding grating 5, and the detector 6 is rotated about an intersection with the optical axis 20 as a rotation center thereby change an angle between each of the phase grating 4, the shielding grating 5 and the detector 6 and the optical axis 20. In FIG. 2, each of the phase grating 4, the shielding grating 5 and the detector 6 is arranged to be orthogonal to the optical axis 20.

In this case, an angle between each of the phase grating 4, the shielding grating 5 and the detector 6 and the optical axis 20 is 90°. In the present exemplary embodiment, 90° serves as the first angle to perform the following description. When the phase grating 4, the shielding grating 5, and the detector 6 are arranged as described above, a center $Q_0$ of an X-ray irradiation area on the shielding grating (hereinafter referred to as a center of the shielding grating. In addition, the X-ray on the optical axis 20 (hereinafter referred to as a central X-ray) is orthogonally incident on the center of the shielding grating is an intersection between the optical axis 20 and the shielding grating) and a center $P_0$ of the X-ray irradiation area on the phase grating (hereinafter referred to as a center of the phase grating. In addition, the center of the phase grating is an intersection between the optical axis 20 and the phase grating). Accordingly, a thickness direction of the phase reference portion or the phase shift portion at the center $P_0$ of the phase grating coincide withes a traveling direction of the X-ray on the optical axis, and similarly, a thickness direction of the shielding portion or the transmission portion at the center $Q_0$ of the shielding grating coincide withes the traveling direction of the central X-ray. Then, the central X-ray incident on the center $Q_0$ of the shielding grating forms a clear-contrast moire on the detector 6. Meanwhile, since an X-ray in an end part of a light beam passing through parts other than the optical axis 20 (hereinafter referred to as a peripheral X-ray 21) is incident obliquely with respect to $P_1$ on the phase grating and $Q_1$ on the shielding grating, the diffraction grating or shielding grating may not perform its original functions, a phase shift amount may varies, or an X-ray that should be transmitted through the diffraction grating or shielding grating may not be transmitted. Similarly, since a peripheral X-ray 22 is incident obliquely with respect to P2 on the phase grating and $Q_2$ on the shielding grating, the phase shift amount may varies, or an X-ray that should be transmitted through the diffraction grating or shielding grating may not be transmitted. As a result, contrast of the moire formed on the detector is degraded as an area is away from the optical axis 20.

In order to obtain the clear contrast at $Q_1$, the shielding grating 5 is rotated by an angle θ about the center $Q_0$ of the shielding grating 5 as a center of rotation from the state of FIG. 2. The angle θ is an amount determined by Equation (2).

$$\theta = \tan^{-1}\left(\frac{Q_0 Q_1}{L_2}\right) \quad (2)$$

In addition, in the present exemplary embodiment, since the shielding grating is rotated about the center $Q_0$ of the shielding grating as a center of rotation, θ is shown using $Q_0 Q_1$, but when the rotation center is not the center of the shielding grating, use of a distance between the rotation center and $Q_1$ instead of $Q_0 Q_1$ in Equation (2) enables θ to be calculated. Since the detector 6 is fixed in parallel to the shielding grating 5, the detector 6 is also rotated by an angle θ about the center of the shielding grating as a center of rotation. Further, the phase grating 4 is also rotated by an angle θ about the center $P_0$ of the X-ray irradiation area, similar to the shielding grating 5. Accordingly, each of the phase grating 4, the shielding grating 5, and the detector 6 forms a (90°−θ) angle with respect to the optical axis 20, as in FIG. 3. In the present exemplary embodiment, (90°−θ) serves as a second angle in the following description. Then, the peripheral X-ray 21 is orthogonally incident on the phase grating 4 and the shielding grating 5 at $P_{11}$ of the phase grating and $Q_{11}$ of the shielding grating.

A peripheral X-ray 21 when the phase grating 4, the shielding grating 5, and the detector 6 are arranged at an angle θ with respect to the optical axis 20 forms a high-contrast moire on the detector similar to the central X-ray when the phase grating 4, the shielding grating 5, and the detector 6 are arranged to be orthogonal to the optical axis 20.

Further, as illustrated in FIG. 3, the phase grating and the shielding grating are kept in parallel even when the phase grating 4, the shielding grating 5, and the detector 6 are tilted with respect to the optical axis. Accordingly, when an X-ray incident on any point $Q_r$ on the shielding grating 5 in the state of FIG. 2 is transmitted through $P_r$ of the phase grating 4, an X-ray directed to the point $Q_r$ passes through the point $P_r$ even in a state of FIG. 3. Since the shielding grating and the detector are fixed in parallel, positions of bright and dark portions in the moire detected by the X-ray detector 6 in the state of FIG. 3 are unchanged from a position detected in the state of FIG. 2. In this case, Equation (1) representing the Talbot condition is not strictly satisfied, but since θ in the X-ray Talbot interferometry is a few degree, degradation of the contrast of the self-image is minute and not an issue.

In the present exemplary embodiment, the phase grating 4, the shielding grating 5 and the detector 6 are rotated while being kept in parallel, to thereby change an angle between each of the phase grating 4, the shielding grating 5 and the detector 6 and the optical axis 20, as described above. Accordingly, an area having good-contrast of the moire can be moved within the light-receiving surface of the detector, with the positions of the bright and dark portions of the moire unchanged. If the area having good-contrast is moved within the light-receiving surface of the detector using above method during the X-ray detection of the detector 6 (during exposure), variations in the contrast within the light-receiving surface of the detector can be reduced. As a result, the contrast of the moire detected from a periphery of the light-receiving surface can be improved over the contrast of the moire in related art. In addition, the related art refers to an imaging apparatus that performs detection of the X-ray only in a state in which the phase grating, the shielding grating, and the detector are arranged as illustrated in FIG. 2. Further, even when the detection of the X-ray may be performed before and after a change in the angle between each of the phase grating, the shielding grating and the detector and the optical axis and a plurality of detection results are combined, the contrast of the moire detected from the periphery of the light-receiving surface can be improved over the related art.

A second exemplary embodiment will be described. The present exemplary embodiment differs from the first exemplary embodiment in that the actuator connected to the phase grating and the actuator connected to the shielding grating move the diffraction grating, the shielding grating, and the detector along the optical axis according to a change in the angle between each of the diffraction grating, the shielding grating and the detector and the optical axis. Accordingly, the more blurring of the self-image can be reduced as compared to the first exemplary embodiment, the more information of the subject with less blurring can be obtained. Hereinafter, a difference between the first exemplary embodiment and the second exemplary embodiment will be described with reference to FIG. 4.

In the first exemplary embodiment, the angle between each of the phase grating 4, the shielding grating 5 and the detector 6 and the optical axis 20 is changed with the phase grating 4, the shielding grating 5 and the detector 6 kept in parallel, and the area having good-contrast of the moire is moved within the light-receiving surface of the detector with the positions of the bright and dark portions of the moire unchanged. However, $P_1$ does not coincide with $P_{11}$, and $Q_1$ does not coincide with $Q_{11}$, as illustrated in FIG. 3. Specifically, an X-ray transmitted through the same position of the subject (here, the peripheral X-ray 21) is incident on different positions (here, $P_1$ and $P_{11}$, and $Q_1$ and $Q_{11}$) of the phase grating and the shielding grating due to rotation of the phase grating and the shielding grating. Accordingly, a phenomenon that the position of the image of the subject 3 on the X-ray detector 6 according to the angle θ is changed (hereinafter referred to as image shift) is generated. If the image shift amount Δx is defined as a distance on the subject 3, a distance between the X-ray source 1 and the subject 3 is L0. According to equation $\Delta x=(Q_0Q_1-Q_0Q_{11})L0/L_2$, $Q_0Q_1=L_2 \tan\theta$, and $Q_0Q_{11}=L_2 \sin\theta$, the image shift amount Δx is represented as Equation (3).

$$\Delta x = L_0(\tan\theta - \sin\theta) \quad \text{Equation (3)}$$

Figure 4:
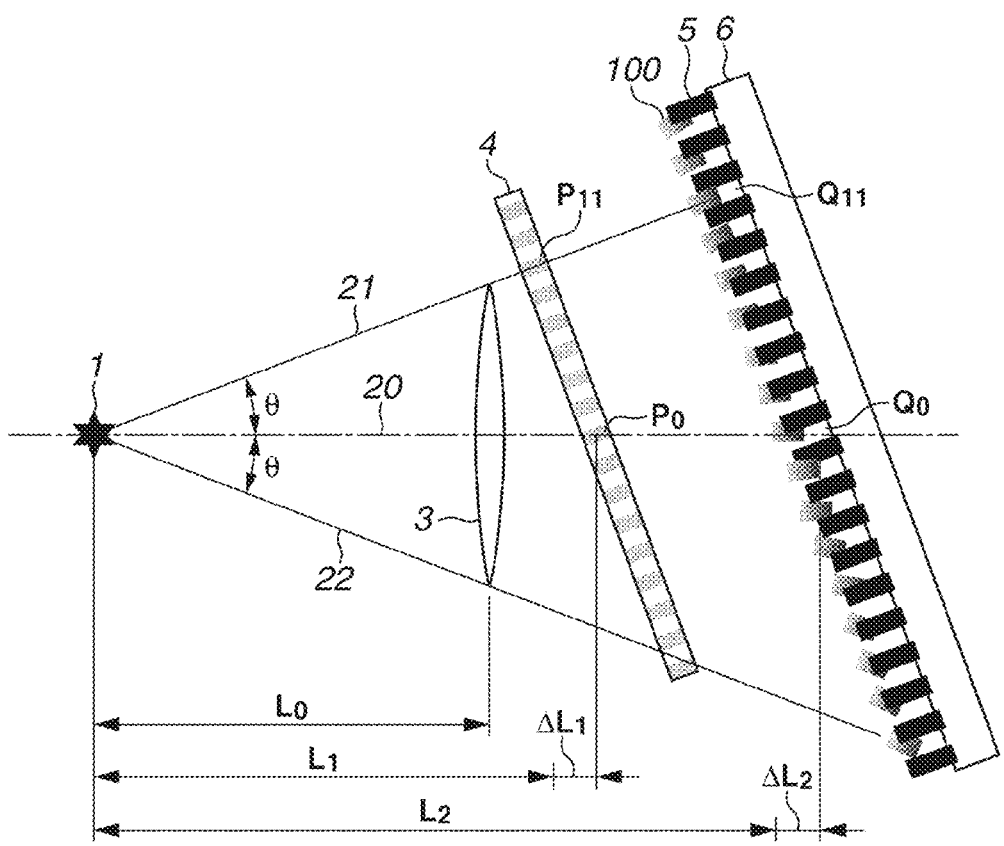
FIG. 4 is a diagram illustrating a principle of a second exemplary embodiment of the present invention.

For example, when L0 is 1000 mm and an subject size is 200 mm, since $\theta=\tan^{-1}(200/2/1000)=5.7°$ in an end part of the subject, an image shift amount Δx is 0.5 mm from Equation (3), which is an amount that is not negligible when a fine structure is observed. In addition, in the arrangement of FIG. 3, a larger amount of image shift is generated in $Q_2$ that is a symmetric position of $Q_1$, but since a moire formed by an X-ray transmitted through the vicinity of $Q_2$ has a low contrast (an amount of the X-ray transmitted through the vicinity of $Q_2$ is low), an influence of the image shift on an obtained detection result is negligible. When the present exemplary embodiment is used, the image shift can be reduced as compared to the first exemplary embodiment. FIG. 4 is a diagram illustrating a principle of reducing the image shift using the present exemplary embodiment. In the present exemplary embodiment, the shielding grating and the phase grating are moved in parallel along the optical axis 20 according to the angle θ from the state illustrated in FIG. 3 in the first exemplary embodiment. A movement amount $\Delta L_2$ of the shielding grating and a movement amount $\Delta L_1$ of the diffraction grating are shown in Equations (4) and (5), respectively.

$$\Delta L_2 = \left(\frac{1}{\cos\theta_2} - 1\right)L_2 \quad (4)$$

$$\Delta L_1 = \left(\frac{1}{\cos\theta_1} - 1\right)L_1 \quad (5)$$

Where an angle $\theta_2$ is an angle between the shielding grating and the optical axis, and an angle $\theta_1$ is an angle between the phase grating and the optical axis. In the present exemplary embodiment, $\theta_1=\theta_2=\theta$.

Similarly, when the shielding grating and the detector are not fixed, a movement amount $\Delta L_3$ of the detector is represented as:

$$\Delta L_3 = \left(\frac{1}{\cos\theta_3} - 1\right)L_3. \quad (6)$$

Where an angle $\theta_3$ is an angle between the detector and the optical axis, and L3 is a distance between the X-ray source and the detector. When the shielding grating and the detector are closely arranged to be nearly in contact with each other as in the present exemplary embodiment, strictly $L_2 \neq L_3$ since the shielding grating has its thickness, but since a difference between $L_2$ and $L_3$ is very small, $L_2$ may be regarded as being equal to $L_3$. If $\theta_2=\theta_3$, $\Delta L_2=\Delta L_3$. A distance $Q_0Q_{11}$ between an intersection $Q_{11}$ between the shielding grating after the parallel movement and the peripheral X-ray 21 and the center $Q_0$ of the shielding grating is represented as Equation (7).

$$Q_0Q_{11}=(L_2+\Delta L_2)\sin\theta=L_2 \tan\theta \quad (7)$$

As can be seen from FIG. 2, since $Q_0Q_1=L_2 \tan\theta$, $Q_0Q_{11}=Q_0Q_1$ and $Q_{11}$ coincide with $Q_1$. Accordingly, image shift does not occur.

Similarly, a distance $P_0P_{11}$ between an intersection $P_{11}$ between the phase grating after the parallel movement and the peripheral X-ray 21 and the center $P_0$ of the phase grating is represented as Equation (8).

$$P_0P_{11}=(L_1+\Delta L_1)\sin\theta=L_1 \tan\theta \quad (8)$$

As can be seen from FIG. 2, since $P_0P_1=L_1 \tan\theta$, $P_0P_{11}=P_0P_1$ and $P_{11}$ coincide with $P_1$. It can be seen from this that an X-ray reaching $Q_1$ of the shielding grating after the parallel movement passes through $P_1$ of the phase grating. Since this is the same as the situation in FIG. 2, the position of the moire formed on the detector 6 is unchanged in the state illustrated in FIG. 2 and the state illustrated in FIG. 4.

As described above, if the shielding grating 5 integrally formed with the detector 6, and the phase grating 4 are moved to simultaneously satisfy Equations (2), (4), and (5), an area having high-contrast of the moire can be arbitrarily selected on the light-receiving surface of the detector with no change in the positions of the bright portion and the dark portion of the moire. Further, the image shift does not occur in the high-contrast place (a position in which the X-ray is incident orthogonally to the detector (the intersection between the peripheral X-ray 21 and the detector in FIG. 4) and its vicinity). Accordingly, the area having good-contrast is moved within the light-receiving surface of the X-ray detector based on the above-described principle during the X-ray detection of the detector 6, enabling the phase image of the subject to be acquired from a result of one detection even when the subject is relatively large. In order to realize this, the X-ray imaging apparatus of the present exemplary embodiment causes the phase grating 4 and the shielding grating 5 to be subjected to the rotation movement and the movement along optical axis described above during the X-ray detection of the detector 6. Further, the detector 6 fixed to the shielding grating are similarly moved.

Further, a method for reducing the image shift as compared to the first exemplary embodiment includes a method for shifting a rotation center for rotation of the phase grating, the shielding grating, and the detector. From the state of FIG. 2, the shielding grating 5 is rotated by θ about the intersection $Q_1$ between the shielding grating 5 and the peripheral X-ray 21. Similarly, the phase grating 4 is rotated by θ about the intersection $P_1$ between the phase grating 4 and the peripheral X-ray 21 as a center of rotation. Then, the peripheral X-ray is incident orthogonally to the phase grating and the shielding grating, with positions in which the peripheral X-ray 21 is incident on the phase grating and the shielding grating being unchanged from the positions of FIG. 2. Thus, the phase grating and the shielding grating are rotated about a position as a center of rotation in which the X-ray is desired to be orthogonally incident to thereby move the rotation centers of the phase grating and the shielding grating on the gratings, thereby enabling a high-contrast place of the moire formed on the detector to be arbitrarily moved. However, with this method, in principle, the X-ray transmitted through the rotation center does not cause the image shift, but the image shift is caused as the position is away from the rotation center. Since the contrast of the moire is degraded as the position is away from the rotation center, an influence of this image shift on the detection result is likely to be negligible. However, the influence of the image shift on the detection result may be considered to be larger, as compared to the method involving the movement along the optical axis described with reference to FIG. 4.

The first exemplary example will be described. In the present example, an example in which simulation has been performed in an X-ray imaging apparatus of the second exemplary embodiment will be described with reference to FIG. 1. FIG. 1 illustrates a configuration of the present example. An X-ray 2 from an X-ray source 1 is transmitted through an subject 3, the X-ray transmitted through the subject 3 is diffracted by a phase grating 4, a part of the self-image formed on the shielding grating 5 is shielded by the shielding grating 5 to form a moire, and the moire is detected by a detector 6. The detector 6 is fixed while keeping in parallel to the shielding grating 5. Further, the detection of the detector 6 is performed according to a signal sent from a detector instruction unit 7 to the detector. Further, a detection result of the detector 6 is sent to a calculator 8 and a differential phase image of the subject is calculated.

The phase grating 4 is rotated about its center as a center of rotation by the actuator 41. Accordingly, an angle between the phase grating and the optical axis is changed and the phase grating is accordingly moved along the optical axis to change a distance with the X-ray source.

Further, similar to the phase grating 4, an angle between each of the shielding grating 5 and the detector 6 and the optical axis and a distance between each of the shielding grating 5 and the detector 6 and the X-ray source is changed by the actuator 51 connected to the shielding grating 5.

Operations of the actuator 41 connected to the phase grating, the actuator 51 connected to the shielding grating and the detector instruction unit 7 are synchronized by the main instruction unit 9.

The present exemplary example will be described in detail based on concrete values in the above configuration. The X-ray 2 generated from the X-ray source 1 has energy of 30 KeV. The X-ray 2 passes through the subject 3 and undergoes phase change according to a refractive index distribution of the subject 3. Then, the X-ray 2 passes through the phase grating 4 and the shielding grating 5 in this order and is incident on the detector 6. The subject 3 is arranged immediately before the phase grating 4 so that an observation area is as wide as possible. However, the subject 3 may also arranged immediately after the phase grating 4, that is, between the phase grating 4 and the shielding grating 5.

A grating region of the phase grating 4 is a square having one side of 120 mm in consideration of a specific part of a person such as a breast or a knee joint being observed at a time. Further, a distance ($L_1$) from the X-ray source 1 to the phase grating 4 is 1000 mm.

Figure 5:
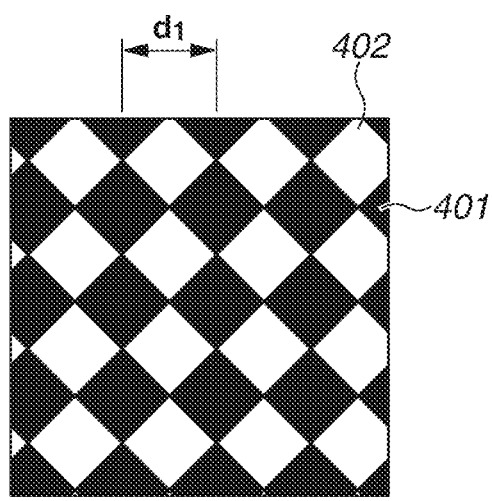
FIG. 5 is a diagram illustrating a part of a pattern of a phase grating according to the first example of the present invention.

A part of the pattern of the phase grating 4 is illustrated in FIG. 5. In the phase grating 4, phase shift portions 401 and phase reference portions 402 are arranged on a checkerboard pattern, and a period that is a distance d1 between centers of the adjacent phase shift portions is 3.0 µm, as illustrated in FIG. 5. Further, in the phase grating 4, convex portions are periodically provided in a grating surface using silicon having a great X-ray transmittance to thereby form the phase shift portions 401 and the phase reference portions 402. Since the phase grating 4 is a π/2 phase grating, the height of the convex portion is a value at which a phase difference between the X-ray passing through the convex portion as the phase shift portion and the X-ray passing through an area between the convex portion as the phase reference portion is π/2. In the present example, since a refractive index difference between silicon and air at an X-ray of 30 KeV is $5.37\times10^{-7}$, the height of the convex portion is 19 µm.

The distance between the phase grating 4 and the shielding grating 5 is 122 mm that is a value of $Z_1$ when, in Equation (1), $Z_0$ is 1000 mm, a wavelength λ of an X-ray of 30 KeV is 0.0413 nm, d is 3 µm, and N is ½. Further, in initial adjustment, the optical axis of the X-ray irradiated from the X-ray source 1 is arranged to pass through the centers of the phase grating 4 and the shielding grating 5, and the central X-ray is caused to be orthogonally incident on the centers.

Figure 6A:
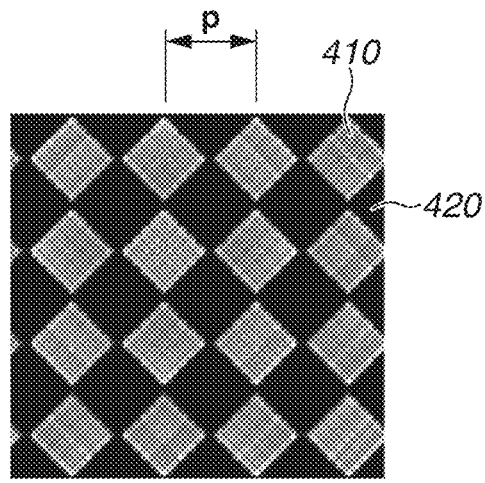
FIG. 6A is a diagram illustrating a part of a self-image according to the first example of the present invention.
Figure 6B:
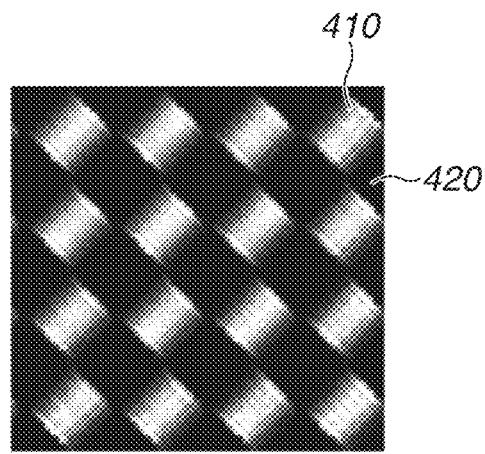
FIG. 6B is a diagram illustrating a part of a self-image according to the first example of the present invention.

FIGS. 6A and 6B illustrate a part of a self-image generated on the shielding grating in such a state. FIG. 6A illustrates a self-image formed around a central portion of the shielding grating, and FIG. 6B illustrates a self-image formed around an upper left end part shielding grating. Bright portions 410 and dark portions 420 of the self-image are arranged in a shape of a checkerboard pattern, and a period p of the self-image is $(Z_0+Z_1)/Z_0\times3$ µm=3.37 µm. In a central portion of the phase grating 4, the X-ray is orthogonally incident on the phase grating 4 and, accordingly, the self-image substantially faithfully reproduces the pattern of the phase grating 4. On the other hand, in a portion away from the center portion of the phase grating, the X-ray is obliquely incident on the phase grating 4 and, accordingly, the self-image is distorted due to an influence of the height of the convex portion of the phase shift portion. In addition, while the π/2 phase grating is adopted in the present example, a π phase grating may be adopted. However, in this case, since the convex portion has a twice height, distortion of the self-image increases.

Figure 7:
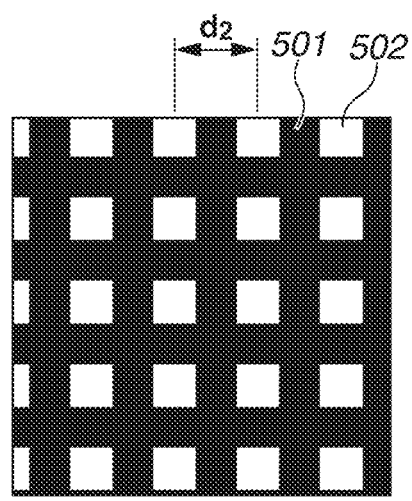
FIG. 7 is a diagram illustrating a part of a pattern of a shielding grating according to the first example of the present invention.

A grating region of the shielding grating 5 is a square having one side of 135 mm from an irradiation area of the X-ray transmitted through the phase grating 4. The material of the shielding grating 5 is gold having great X-ray absorption rate. Convex portions are periodically provided on a surface so that the X-ray transmittance is periodically changed. The height of the convex portion is 60 µm from an extinction coefficient of $1.65\times10^{-7}$ of the gold in an X-ray of 30 KeV so that an intensity ratio of the X-ray passing through the convex portion and the X-ray passing between the convex portions is 0.05. In a pattern of the shielding grating 5, shielding portions 501 and transmission portions 502 are arranged in a grid pattern as illustrated in FIG. 7, and a ratio of a width of the shielding portion and a width of the transmission portion is 1:1. In addition, the shielding portion is a portion in which the convex portion is formed, and the transmission portion is a portion between the convex portions. A period of the shielding grating is slightly changed from the period of the self-image to thereby generate a moire having a greater period than the resolution of the detector 6. In the present example, a period d2 of the shielding grating 5 is 3.51 µm in order to generate a moire having a period of 80 µm. In addition, when the pixel period of the detector 6 is 20 µm, the moire period corresponds to four pixels of the detector and is suitable for analysis using the above Fourier transform method.

In the imaging apparatus of the present exemplary example, when the X-ray source, the phase grating, and the shielding grating are arranged in the above initial adjustment positions, a slope of the incident X-ray in an end part of the grating region of the shielding grating 5 is (135 mm/2)/(1000 mm+122 mm)=67.5/1122, and the height of the convex portion is 60 µm. In addition, here, the end part refers to an end part in any of up, down, left and right directions, not four corners. From the incident X-ray and the height of the convex portion, an X-ray that should be originally transmitted through the shielding grating may not pass through the transmission portion at least in an end part of the grating region of the shielding grating 5 and, as a result, the contrast of the moire is degraded as an area is away from the optical axis.

Figure 8:
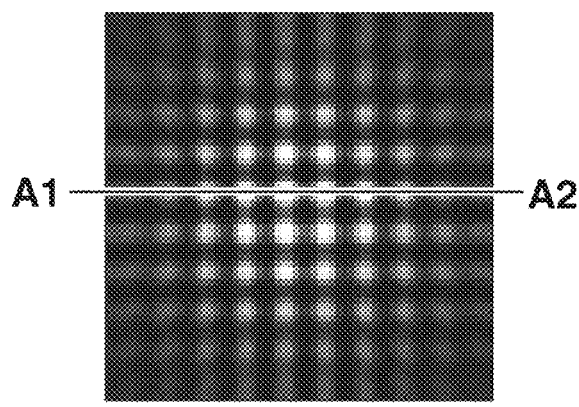
FIG. 8 is a diagram illustrating a moire according to the first example of the present invention.
Figure 9:
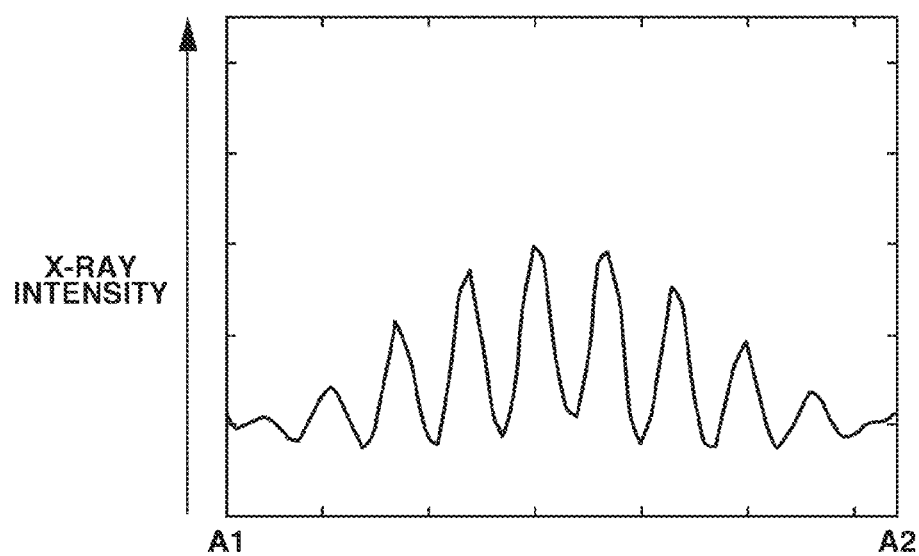
FIG. 9 is a diagram illustrating an intensity distribution on a horizontal straight line passing through a center of the moire of FIG. 8.

FIG. 8 illustrates a simulation result of the moire detected by the detector 6 in a state in which the X-ray source, the phase grating, and the shielding grating are arranged in the initial adjustment positions, i.e., the X-ray is incident orthogonally to the center of the phase grating 4 and the center of the shielding grating 5. However, the subject is not put and a pixel size of the detector is 2.1 mm due to limitations of simulation, and further a moire having a period of 15 mm is generated so that the distribution of the contrast is easily recognized. FIG. 9 illustrates an intensity distribution on a horizontal straight line A1-A2 passing through the vicinity of a center of the image illustrated in FIG. 8, in which a vertical axis indicates intensity and a horizontal axis indicates a position. FIG. 9 illustrates that the contrast of the moire is clear near an intersection with the optical axis, but the contrast of the moire becomes unclear as a position is away from the optical axis.

Figure 10A:
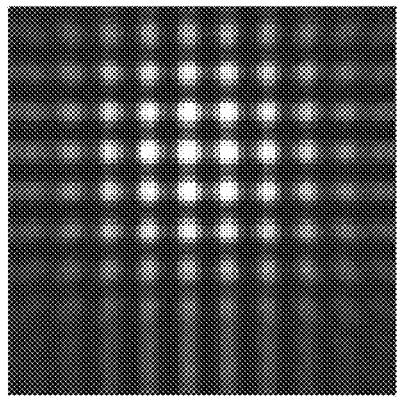
FIG. 10A is a diagram illustrating a moire according to the first example of the present invention.
Figure 10B:
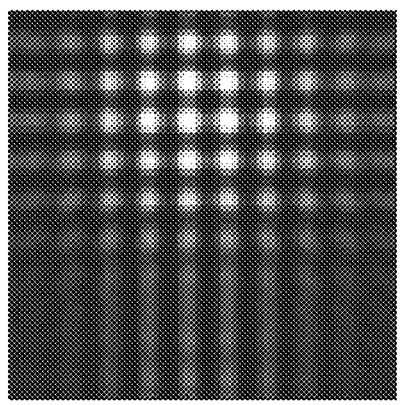
FIG. 10B is a diagram illustrating a moire according to the first example of the present invention.
Figure 10C:
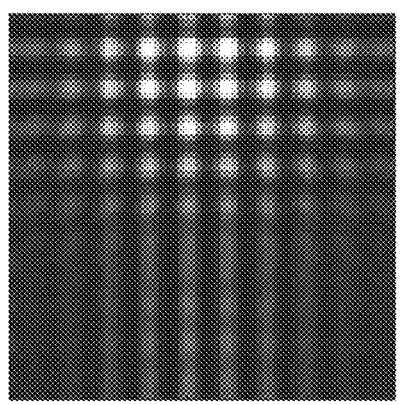
FIG. 10C is a diagram illustrating a moire according to the first example of the present invention.
Figure 11:
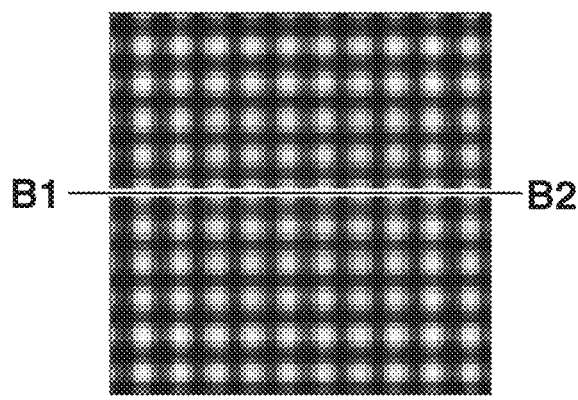
FIG. 11 is a diagram illustrating an average image according to the first example of the present invention.

In order to describe FIGS. 10 and 11, gratings region or a light-receiving surface area of the phase grating, the shielding grating, and the detector is represented as an xy coordinate. A coordinate of each center is (0,0), a coordinate of each upper end part is (0,1), and a coordinate of each right end part is (1,0).

FIG. 10A illustrates a simulation result of a moire detected when an angle between each of the phase grating 4, the shielding grating 5 and the detector 6 and the optical axis is changed so that the X-ray is incident orthogonally to a position expressed as (0,⅜) in each of the phase grating, the shielding grating, and the detector.

Similarly, FIG. 10B illustrates a simulation result of a moire detected when the X-ray is caused to be incident orthogonally to a position expressed as (0,⅔) in each of the phase grating, the shielding grating, and the detector, and FIG. 10C illustrates a simulation result of a moire detected when the X-ray is caused to be incident orthogonally to a position expressed as (0,⅛) in each of the phase grating, the shielding grating, and the detector.

In order to detect the moires illustrated in FIGS. 10A, 10B and 10C, the phase grating 4, the shielding grating 5, and the detector 6 may be moved based on Equations (2), (4) and (5) as follows. In addition, a movement of the phase grating 4, the shielding grating 5, and the detector 6 is performed by the actuator 41 connected to the phase grating and the actuator 51 connected to the shielding grating.

First, in order to detect the moire illustrated in FIG. 10A, the phase grating 4 and the shielding grating 5 are rotated by 1.72° about centers of the gratings as a center of rotation so that upper portions of the gratings are close to the X-ray source. Since the detector is fixed in parallel to the shielding grating, the detector is also rotated as the shielding grating rotates. Through this rotation, the angle between each of the phase grating, the shielding grating and the detector and the optical axis becomes 88.28°. Together with rotation of the gratings, the phase grating is moved 0.45 mm and the shielding grating and the detector are moved 0.51 mm in a direction away from the X-ray source along the optical axis.

Similarly, in order to detect the moire illustrated in FIG. 10B, the phase grating and the shielding grating are rotated by 3.43° about centers of the gratings as a rotation center so that the upper portions of the gratings are close to the X-ray source. Accordingly, the angle between each of the phase grating, the shielding grating and the detector and the optical axis is 86.57°. Together with this rotation, the phase grating 4 is moved 1.79 mm and the shielding grating and the detector is moved 2.01 mm in the direction away from the X-ray source along the optical axis.

Similarly, in order to detect the moire illustrated in FIG. 10C, the phase grating and the shielding grating are rotated by 5.14° about the centers of the gratings as a rotation center so that the upper portions of the gratings are close to the X-ray source. Accordingly, the angle between each of the phase grating, the shielding grating and the detector and the optical axis is 84.86°. Together with this rotation, the phase grating is moved 4.04 mm and the shielding grating and the detector are moved 4.53 mm in the direction away from the X-ray source along the optical axis.

It can be seen from comparison between FIG. 8 and FIGS. 10A, 10B and 10C that a clear contrast place is moved, but positions of the bright portion and the dark portion remain unchanged.

Next, respective moires detected when the X-ray is orthogonally incident at nine points expressed as (0,0), (0,±⅜), (±⅜,0), and (±⅜,±⅜) in each of the phase grating 4, the shielding grating 5 and the detector 6 are obtained through simulation. In addition, the simulation is performed using Equations (2), (4) and (5) supposing that the phase grating, the shielding grating and the detector are rotationally moved and moved along the optical axis to prevent the image shift so that the X-ray is orthogonally incident at the respective points. An average image of a total of nine acquired moires is illustrated in FIG. 11.

Figure 12:
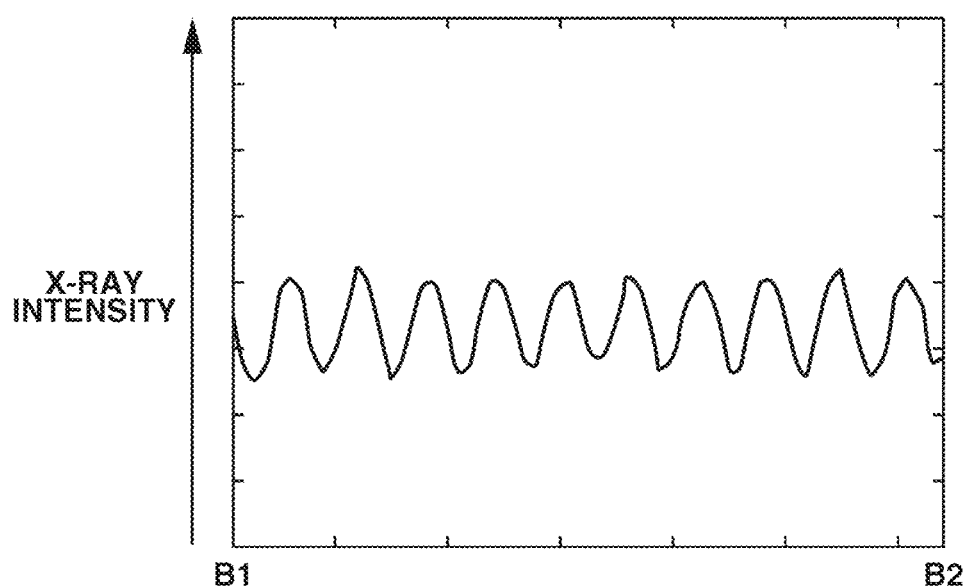
FIG. 12 is a diagram illustrating an intensity distribution on a horizontal straight line passing through a center of the average image of FIG. 11.

FIG. 12 illustrates an intensity distribution on a horizontal straight line B1-B2 passing through a center of the image illustrated in FIG. 11. A vertical axis indicates intensity and a horizontal axis indicates a position. FIG. 12 illustrates that a substantially uniform contrast can be obtained on an entire surface between B1 and B2. Accordingly, when the phase grating 4, the shielding grating 5 and the detector 6 are moved as described above (moved to satisfy Equations 2, 4 and 5) during the X-ray detection of the detector 6 (during the exposure), a moire pattern having homogenized contrast can be obtained with one image.

Here, an average of the moires when the angle between each of the phase grating 4, the shielding grating 5 and the detector 6 and the optical axis is changed so that the X-ray is orthogonally incident on the phase grating 4, the shielding grating 5 and the detector 6 at the nine points is illustrated. However, it is understood that moire homogenization is achieved when the number of angles between each of the phase grating 4, the shielding grating 5 and the detector 6 and the optical axis increases at the time of the detection. More ideally, the detection may be performed while two-dimensionally continuously changing the angle between each of the phase grating 4, the shielding grating 5 and the detector 6 and the detector.

Hereinafter, a subject imaging procedure in the present exemplary example will be described with reference to FIG. 1.

Step 1: A detection time of the X-ray of the detector 6, and a movement pattern of an area on the detector on which the X-ray is orthogonally incident during the X-ray detection are inputs to the main instruction unit 9.

Step 2: A light receiving start signal is sent from the main instruction unit 9 to the detector instruction unit 7 to thereby start the detection of the X-ray 2 of the detector 6.

Step 3: A movement amount instruction value is sent from the main instruction unit 9 to the actuators 41 and 51 connected to the phase grating and the shielding grating so that the phase grating 4 and the shielding grating 5 move while satisfying Equations (2), (4) and (5) to realize the movement pattern input in step 1. The actuators 41 and 51 connected to the phase grating and the shielding grating, respectively, move the phase grating, the shielding grating, and the detector fixed to the shielding grating according to the received instructed value.

Step 4: A detection end signal is sent from the main instruction unit 9 to the detector instruction unit 7 to thereby end the detection of the X-ray of the detector 6, and the moire detected by the detector 6 is sent to the calculator 8 via the detector instruction unit 7.

Step 5: The calculator 8 calculates a differential phase image of the subject 3 from the moire using the fast Fourier transform (FFT) method. Further, the differential phase image is integrated to calculate a phase image of the subject 3.

With the X-ray imaging apparatus of the present exemplary example, the contrast of the moire in other areas than near the intersection between the optical axis and the detector can be improved over related art by executing the above steps. In related art, the moire may be blurred according to the aspect ratio of the phase grating and the distance from the optical axis. Further, the X-ray that should be transmitted through the shielding grating is almost not transmitted according to the aspect ratio of the shielding grating and the distance from the optical axis and it is difficult to acquire a differential phase image of the subject. However, in the present example, the angle between each of the phase grating, the shielding grating and the detector and the optical axis is changed to enable the X-ray to be orthogonally incident on the phase grating and the shielding grating even in a position away from the optical axis, thereby reducing such a problem. Accordingly, since a range of moire obtained by one detection is wider than the range of related art, the imaging range can be increased.

Figure 13:
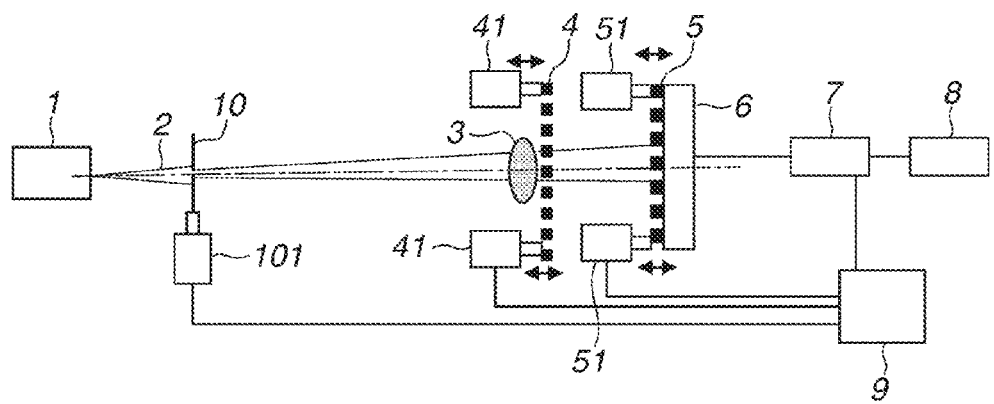
FIG. 13 is a diagram illustrating an X-ray imaging apparatus according to a second example of the present invention.

A second exemplary example will be described. The second exemplary example of the second exemplary embodiment will be described with reference to FIGS. 13 and 14. FIG. 13 illustrates a configuration of the present exemplary example, which differs from the first exemplary example in that an X-ray mask 10 and an actuator 101 as an X-ray mask moving unit connected to the X-ray mask are included between an X-ray source and a subject. Further, only parts of the present exemplary example different from the first exemplary example will be described.

Figure 14:
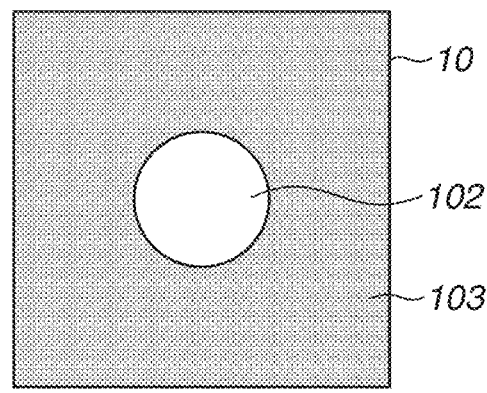
FIG. 14 is a diagram illustrating a structure of an X-ray mask according to the second example of the present invention.

FIG. 14 illustrates a structure of the X-ray mask. The X-ray mask 10 includes a transmission portion 102 (hollow region) that transmits an X-ray and a shielding portion that shields the X-ray 103. Since the X-ray mask 10 is arranged between the X-ray source 1 and the subject 3, only the X-ray incident on the transmission portion 102 among the X-rays emitted from the X-ray source 1 is radiated to the subject 3 and reaches an X-ray detector 6. The actuator 101 connected to the X-ray mask receives an instruction from a main instruction unit 9 to change a position of the X-ray mask 10.

The main instruction unit 9 sends an instruction signal to the actuator 101 connected to the X-ray mask to move the X-ray mask 10 so that the X-ray orthogonally incident on the shielding grating 5 typically passes through the transmission portion 102 of the X-ray mask, advantageously, a center.

The X-ray orthogonally incident on the shielding grating 5 is an X-ray that generates a clear-contrast moire, which passes through the subject 3 and reaches the detector 6. Meanwhile, an X-ray away from the X-ray orthogonally incident on the shielding grating 5, i.e., an X-ray obliquely incident on the shielding grating 5 to a certain extent or more is shielded by the X-ray mask 10 and does not reach the detector 6 as well as the subject 3. In this case, "to a certain extent or more" is determined by a size of the transmission portion 102 of the X-ray mask and a position at which the X-ray orthogonally incident on the shielding grating is transmitted through the transmission portion 102.

In this state, when the phase grating 4, the shielding grating 5, and the detector 6 are moved along the optical axis while changing an angle between each of the phase grating 4, the shielding grating 5 and the detector 6 and the optical axis by moving the phase grating 4, the shielding grating 5, and the detector 6, similar to the first exemplary example, the subject 3 is not radiated with the X-ray in a unclear contrast area. Accordingly, a radiation exposure amount of the subject can be reduced as compared to the first exemplary example. Further, since in an unclear-contrast area, the X-ray does not reach the detector, the moire may not be obtained in the area. Accordingly, since only an X-ray that forms a moire in a clear contrast state is detected by the detector, an image of a good-contrast moire can be obtained as compared to the first exemplary example.

Figure 15:
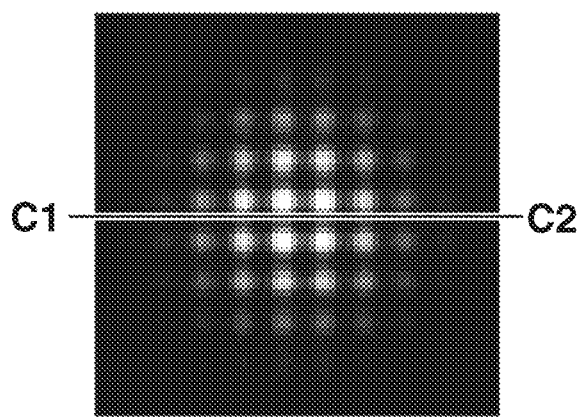
FIG. 15 is a diagram illustrating a moire according to the second example of the present invention.
Figure 16:
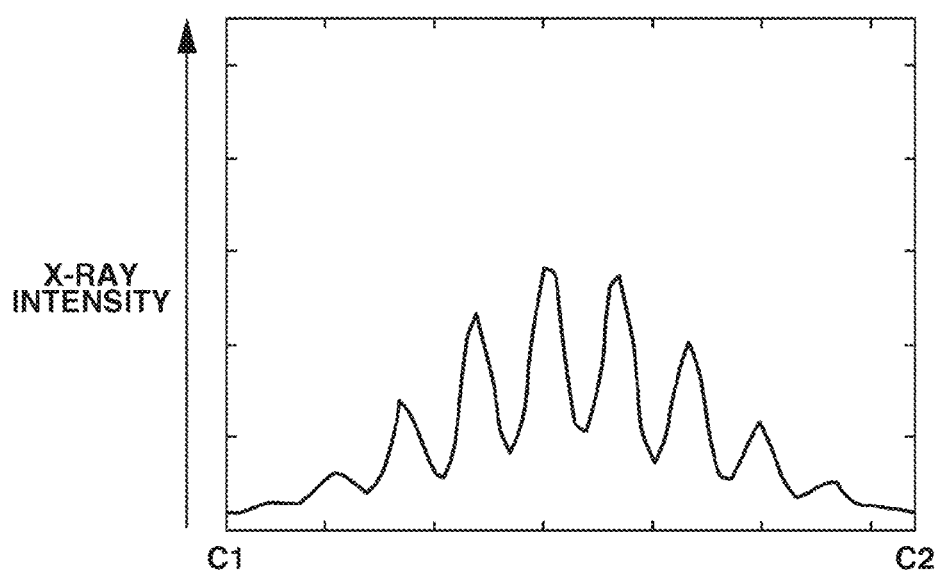
FIG. 16 is a diagram illustrating an intensity distribution on a horizontal straight line passing through a center of an image of FIG. 15.

Further, the X-ray transmittance may be gradually changed in a boundary between the transmission portion 102 and the shielding portion 103 of the X-ray mask 10. Accordingly, even when a movement of an area on which the X-ray is incident orthogonally to the phase grating and the shielding grating is low, it is not likely that the boundary between the transmission portion 102 and the shielding portion 103 appears in the moire of the detection result. FIG. 15 illustrates a result of simulating, in the same condition as in FIG. 8, a moire when an X-ray is orthogonally incident on the center of the phase grating and the center of the shielding grating. In this case, a transmittance distribution of the transmission portion 102 of the X-ray mask 10 has a Gaussian form in which a radius at which the transmittance becomes 1/e is converted into a size of the X-ray detector 6 and becomes ⅜ of the size. FIG. 16 illustrates an intensity distribution on a horizontal straight line C1C2 passing through a center of the image illustrated in FIG. 15. It can be seen from a comparison with FIG. 9 that the intensity of the X-ray is reduced in an area outside a certain range about an intersection between the optical axis and the detector.

Figure 17:
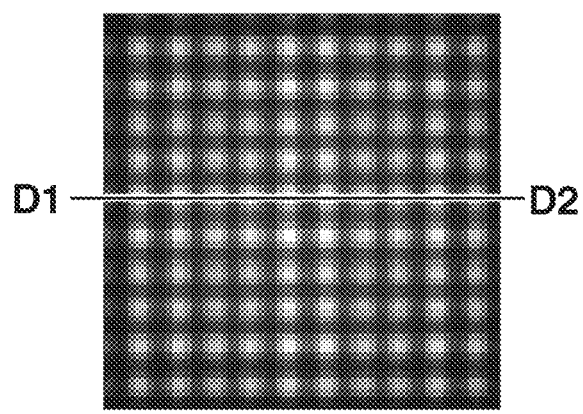
FIG. 17 is a diagram illustrating an average image according to the second example of the present invention.
Figure 18:
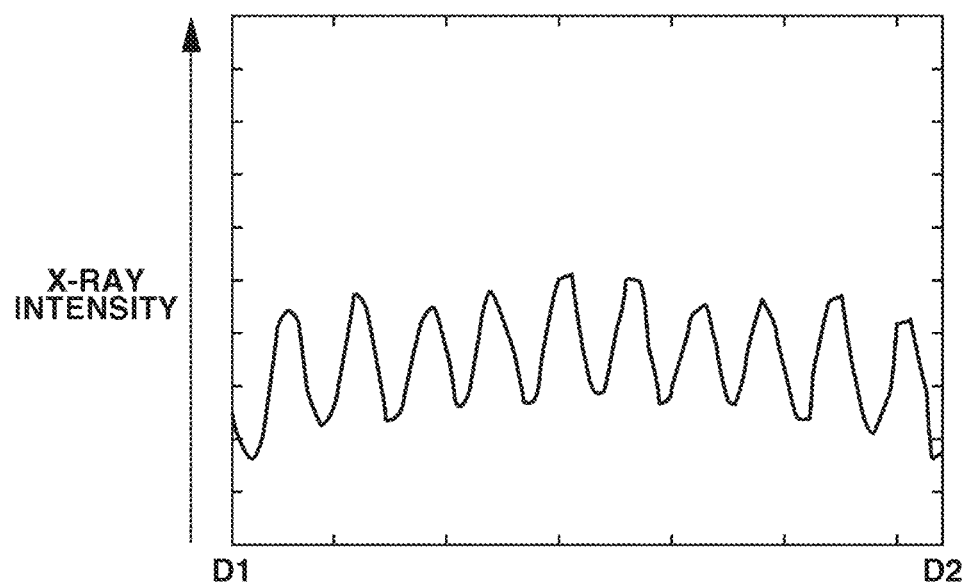
FIG. 18 is a diagram illustrating an intensity distribution on a horizontal straight line passing through a center of the average image of FIG. 17.

FIG. 17 illustrates an average image of nine moire patterns obtained through the same simulation as the simulation of FIG. 11 in the first example. FIG. 18 illustrates an intensity distribution on a horizontal straight line D1D2 passing through a center of the image illustrated in FIG. 17. It can be seen that entire contrast is improved over the contrast illustrated in FIG. 12 in the first example.

While the exemplary embodiments of the present invention have been described above, the present invention is not limited to the exemplary embodiments and various changes and modifications may be made without departing from the scope and spirit of the present invention. For example, the shielding grating and the detector may not be fixed to each other and may be moved by respective actuators connected to the shielding grating and the detector. Alternatively, the phase grating, the shielding grating and the detector may be fixed to one another and moved by one actuator.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2011-201819 filed Sep. 15, 2011, which is hereby incorporated by reference herein in its entirety.

What is claimed is:

1. An X-ray imaging apparatus for imaging a subject, the X-ray imaging apparatus comprising:
a diffraction grating configured to form an interference pattern by diffracting X-ray radiation from an X-ray source;
a shielding grating configured to block part of the interference pattern;
a detector configured to detect the X-ray radiation passing through the shielding grating; and
a moving unit configured to change an angle of each of the diffraction grating, the shielding grating and the detector with respect to an optical axis,
wherein the detector is configured to detect the X-ray radiation passing through the shielding grating according to a change in the angle between the optical axis and at least one of the diffraction grating, the shielding grating and the detector, and
wherein the moving unit is configured to change a distance from each of the diffraction grating, the shielding grating and the detector to the X-ray source according to a change in the angle of each of the diffraction grating, the shielding grating and the detector with respect to the optical axis.

2. The X-ray imaging apparatus according to claim 1, wherein the X-ray radiation from the radiation source includes a divergent beam incident on the diffraction grating.

3. The X-ray imaging apparatus according to claim 1, wherein the moving unit is configured to change the angle of each of the diffraction grating, the shielding grating and the detector with respect to the optical axis by moving the diffraction grating, the shielding grating and the detector.

4. The X-ray imaging apparatus according to claim 1, wherein the moving unit is configured to change the angle of each of the diffraction grating, the shielding grating and the detector with respect to the optical axis from a first angle to a second angle different from the first angle, and
wherein the detector is configured, at least when each of the diffraction grating, the shielding grating and the detector forms the first angle with respect to the optical axis, and when each of the diffraction grating, the shielding grating and the detector forms the second angle with respect to the optical axis, to detect the X-ray radiation passing through the shielding grating.

5. The X-ray imaging apparatus according to claim 1, wherein the moving unit is configured to change the angle of each of the diffraction grating, the shielding grating and the detector with respect to the optical axis during the detection of the X-ray radiation passing through the shielding grating by the detector.

6. The X-ray imaging apparatus according to claim 1, wherein the moving unit changes the distance from the diffraction grating to the X-ray source by $\Delta L_1$, the distance from the shielding grating to the X-ray source by $\Delta L_2$, and the distance from the detector to the X-ray source by $\Delta L_3$ along the optical axis according to a change in the angle of each of the diffraction grating, the shielding grating and the detector with respect to the optical axis,
wherein, when an angle between the diffraction grating and the optical axis is $\theta_1$, and a distance from the diffraction grating to the X-ray source is $L_1$, Equation 1 is satisfied:

$$\Delta L_1 = \left(\frac{1}{\cos\theta_1} - 1\right)L_1. \quad \text{[Equation 1]}$$

7. The X-ray imaging apparatus according to claim 6, wherein, when an angle between the shielding grating and the optical axis is $\theta_2$, and a distance from the shield grating to the X-ray source is $L_2$, Equation 2 is satisfied:

$$\Delta L_2 = \left(\frac{1}{\cos\theta_2} - 1\right)L_2. \quad \text{[Equation 2]}$$

8. The X-ray imaging apparatus according to claim 6, wherein, when the angle between the detector and the optical axis is $\theta_3$, and a distance from the detector to the X-ray source is $L_3$, Equation 3 is satisfied:

$$\Delta L_3 = \left(\frac{1}{\cos\theta_3} - 1\right)L_3. \quad \text{[Equation 3]}$$

9. The X-ray imaging apparatus according to claim 1, wherein the moving unit is configured to change at least one of an angle between the diffraction grating and the optical axis by rotating the diffraction grating about a rotation center on the diffraction grating as a center, an angle between the shielding grating and the optical axis by rotating the shielding grating about a rotation center on the shielding grating as a center, and an angle between the detector and the optical axis by rotating the detector about a rotation center on the detector as a center,
wherein the rotation center on the diffraction grating moves on the diffraction grating according to a change in the angle between the diffraction grating and the optical axis,
wherein the rotation center on the shielding grating moves on the shielding grating according to a change in the angle between the shielding grating and the optical axis, and
wherein the rotation center on the detector moves on the detector according to a change in the angle between the detector and the optical axis.

10. The X-ray imaging apparatus according to claim 1, further comprising:
an X-ray mask including a transmission portion configured to transmit the X-ray radiation and a shielding portion configured to shield part of the X-ray radiation; and
an X-ray mask moving unit configured to move the X-ray mask,
wherein the X-ray mask is arranged between the X-ray source and the subject, and
wherein the X-ray mask moving unit moves the X-ray mask according to an angle between the shielding grating and the optical axis so that an X-ray incident orthogonal to the shielding grating among the X-ray radiation passes through the transmission portion of the X-ray mask.

11. The X-ray imaging apparatus according to claim 1, wherein the moving unit is configured to change the angle of each of the diffraction grating, the shielding grating and the detector with respect to the optical axis so that a peripheral X-ray passing through a part other than the optical axis is incident orthogonal to at least one of the diffraction grating, the shielding grating and the detector.

12. The X-ray imaging apparatus according to claim 1, further comprising a calculator configured to calculate information about a change in the X-ray radiation passing through the subject.

13. The X-ray imaging apparatus according to claim 12, wherein the calculator calculates the information from respective detection results of the X-ray radiation before and after the change.

14. The X-ray imaging apparatus according to claim 1, wherein the moving unit is configured to change a distance from each of the diffraction grating, the shielding grating and the detector to the X-ray source by moving the diffraction grating, the shielding grating and the detector along the optical axis.

15. The X-ray imaging apparatus according to claim 1, wherein when the detector detects the X-ray radiation, the diffraction grating, the shielding grating, and the detector are arranged in parallel.

* * * * *